(12) United States Patent
Iaccino et al.

(10) Patent No.: US 8,937,205 B2
(45) Date of Patent: *Jan. 20, 2015

(54) PROCESS FOR THE PRODUCTION OF XYLENES

(75) Inventors: Larry L. Iaccino, Seabrook, TX (US); Glenn C. Wood, Houston, TX (US); Jesus A. Ramos, Houston, TX (US); Lane L. McMorris, The Woodlands, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/465,766

(22) Filed: May 7, 2012

(65) Prior Publication Data

US 2013/0296624 A1 Nov. 7, 2013

(51) Int. Cl.
*C07C 2/66* (2006.01)
*C07C 2/64* (2006.01)
*C07C 2/86* (2006.01)

(52) U.S. Cl.
CPC .. *C07C 2/64* (2013.01); *C07C 2/864* (2013.01)
USPC .......... 585/321; 585/322; 585/323; 585/446; 585/474; 585/470; 585/475

(58) Field of Classification Search
USPC ......... 585/319, 321–323, 470, 483, 486, 474; 208/50, 51, 53, 58, 62, 66, 67
See application file for complete search history.

(56) References Cited

U.S. PATENT DOCUMENTS

| | | | |
|---|---|---|---|
| 2,415,272 A * | 2/1947 | Benedict et al. | 208/70 |
| 3,409,540 A | 11/1968 | Gould et al. | |
| 3,862,898 A | 1/1975 | Boyd et al. | |
| 3,894,934 A | 7/1975 | Owen et al. | |
| 4,053,388 A | 10/1977 | Bailey | |

(Continued)

FOREIGN PATENT DOCUMENTS

| | | |
|---|---|---|
| AU | 776 247 | 9/2004 |
| EP | 0136072 | 4/1985 |

(Continued)

OTHER PUBLICATIONS

U.S. Appl. No. 61/421,917, filed Dec. 10, 2010, Ellrich et al.

(Continued)

*Primary Examiner* — Thuan D Dang

(57) ABSTRACT

A hydrocarbon upgrading process is described in which a hydrocarbon feed is treated in at least one of a steam cracker, catalytic cracker, coker, hydrocracker, and reformer under suitable conditions to produce a first stream comprising aliphatic and aromatic hydrocarbons. A second stream comprising $C_6$-$C_9$ aliphatic and aromatic hydrocarbons is recovered from the first stream and aliphatic hydrocarbons are removed from at least part of the second stream to produce an aliphatic hydrocarbon-depleted stream. The aliphatic hydrocarbon-depleted stream is then dealkylated and/or transalkylated and/or cracked (D/T/C) by contact with a catalyst under suitable reaction conditions to produce a third stream having an increased benzene and/or toluene content compared with said aliphatic hydrocarbon-depleted stream and a light paraffin by-product. Benzene and/or toluene from the third stream is then methylated with a methylating agent to produce a xylene-enriched stream.

18 Claims, 1 Drawing Sheet

(56) References Cited

U.S. PATENT DOCUMENTS

| | | | |
|---|---|---|---|
| 4,058,450 A | 11/1977 | Le Page et al. | |
| 4,058,454 A | 11/1977 | Asselin | |
| 4,078,990 A * | 3/1978 | Brennan et al. | 208/64 |
| 4,257,871 A | 3/1981 | Wernicke et al. | |
| 4,980,053 A | 12/1990 | Li et al. | |
| 5,043,502 A | 8/1991 | Martindale et al. | |
| 5,232,675 A | 8/1993 | Shu et al. | |
| 5,326,465 A | 7/1994 | Yongqing et al. | |
| 5,358,918 A | 10/1994 | Yukang et al. | |
| 5,380,690 A | 1/1995 | Zhicheng et al. | |
| 5,932,777 A | 8/1999 | Sughrue et al. | |
| 6,077,984 A | 6/2000 | Drake et al. | |
| 6,080,698 A | 6/2000 | Zhang et al. | |
| 6,114,592 A * | 9/2000 | Gajda et al. | 585/475 |
| 6,153,089 A | 11/2000 | Das et al. | |
| 6,210,562 B1 | 4/2001 | Xie et al. | |
| 6,211,104 B1 | 4/2001 | Shi et al. | |
| 6,342,153 B1 | 1/2002 | Guan et al. | |
| 6,420,621 B2 | 7/2002 | Sha et al. | |
| 6,423,879 B1 | 7/2002 | Brown et al. | |
| 6,504,073 B1 * | 1/2003 | Ushio et al. | 585/475 |
| 6,635,792 B2 | 10/2003 | Choi et al. | |
| 6,740,788 B1 * | 5/2004 | Maher et al. | 585/319 |
| 7,119,239 B2 * | 10/2006 | Johnson et al. | 585/467 |
| 7,153,478 B2 | 12/2006 | Xu et al. | |
| 7,176,339 B2 | 2/2007 | Iaccino et al. | |
| 7,179,434 B1 | 2/2007 | Maher et al. | |
| 7,288,687 B1 * | 10/2007 | Frey et al. | 585/319 |
| 7,297,831 B2 | 11/2007 | Lee et al. | |
| 7,301,063 B2 | 11/2007 | Choi et al. | |
| 7,396,967 B2 | 7/2008 | Iaccino et al. | |
| 7,553,791 B2 * | 6/2009 | McMinn et al. | 502/64 |
| 7,563,358 B2 | 7/2009 | Stavens et al. | |
| 7,578,929 B2 | 8/2009 | Stell et al. | |
| 7,601,311 B2 * | 10/2009 | Casey et al. | 422/234 |
| 7,629,498 B2 | 12/2009 | Brown et al. | |
| 7,727,490 B2 * | 6/2010 | Zhou | 422/609 |
| 7,923,399 B2 | 4/2011 | Long et al. | |
| 7,939,702 B2 | 5/2011 | Choi et al. | |
| 7,972,498 B2 | 7/2011 | Buchanan et al. | |
| 8,183,424 B2 | 5/2012 | Levin et al. | |
| 2001/0053868 A1 | 12/2001 | Chester et al. | |
| 2002/0092797 A1 | 7/2002 | Choi et al. | |
| 2003/0105372 A1 | 6/2003 | Feng et al. | |
| 2003/0116471 A1 | 6/2003 | Zhang et al. | |
| 2004/0015027 A1 | 1/2004 | Iaccino et al. | |
| 2004/0049093 A1 | 3/2004 | Cheung et al. | |
| 2005/0020867 A1 | 1/2005 | Xie et al. | |
| 2005/0209495 A1 | 9/2005 | McCoy et al. | |
| 2006/0194996 A1 | 8/2006 | Umansky et al. | |
| 2008/0051615 A1 | 2/2008 | Stavens | |
| 2008/0249345 A1 | 10/2008 | Kin et al. | |
| 2009/0000988 A1 | 1/2009 | Brown et al. | |
| 2010/0040517 A1 | 2/2010 | Brown et al. | |
| 2012/0149958 A1 | 6/2012 | Ellrich et al. | |

FOREIGN PATENT DOCUMENTS

| | | |
|---|---|---|
| EP | 1068166 | 3/2004 |
| KR | 10-0632571 | 10/2006 |
| WO | WO 01/79383 | 10/2001 |
| WO | WO 02/44306 | 6/2002 |
| WO | WO 2007/108573 | 9/2007 |
| WO | WO 2012/015541 | 2/2012 |

OTHER PUBLICATIONS

U.S. Appl. No. 13/465,766, filed May 7, 2012, Iaccino et al.

\* cited by examiner

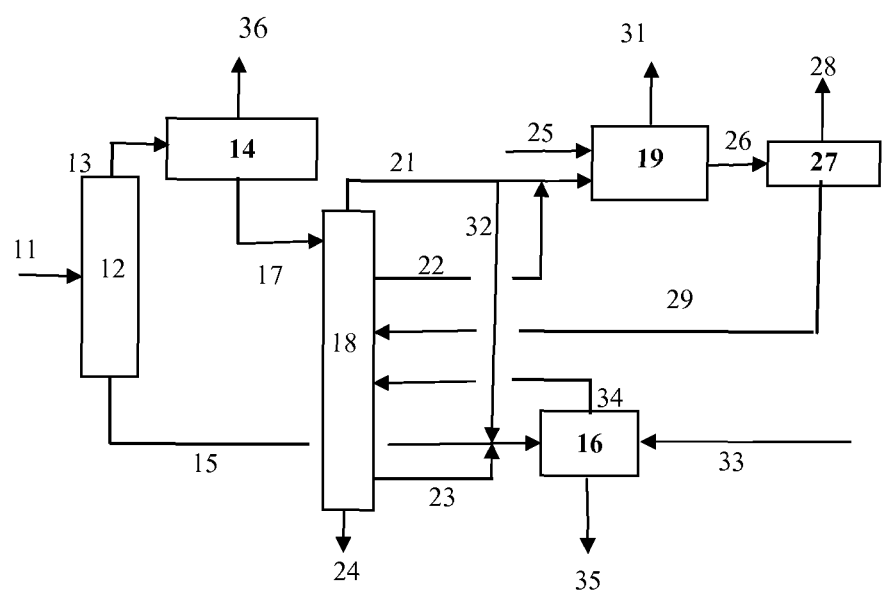

PROCESS FOR THE PRODUCTION OF XYLENES

STATEMENT OF RELATED CASES

This application is related to U.S. Ser. No. 13/303,855, filed Nov. 23, 2011 which claims the benefit of and priority to U.S. Ser. No. 61/421,917 filed Dec. 10, 2010.

FIELD OF THE INVENTION

The invention relates to a process for the production of xylenes from naphtha feedstocks.

BACKGROUND OF THE INVENTION

Xylene isomers find wide and varied application. They are especially valuable as intermediates in chemical processes. By way of example, para-xylene (PX) is a feedstock for terephthalic acid, which is used in the manufacture of polyester fibers and films, meta-xylene (MX) is used in the manufacture of dyes, and ortho-xylene (OX) is used as a feedstock for phthalic anhydride, which itself is used in the manufacture of plasticizers. PX is currently the most valuable of the xylene isomers and, although research related to obtaining (e.g., producing or purifying) PX is too voluminous to mention, there is still intensive research in the area.

There are many possible feeds currently used to obtain PX. The majority of para-xylene produced today comes from catalytic reforming, which involves dehydrogenation and dehydrocyclization of naphtha feedstocks. The effluent of the reforming process, known as reformate, is rich in aromatics, particularly benzene, toluene and mixed xylenes (BTX), and is used as feedstock to many aromatics plants. Processes exist to increase the yield of para-xylene over the equilibrium mixture in the reformate, including selective toluene disproportionation and selective methylation of benzene and/or toluene with methanol.

Recently, significant research has focused on finding alternative sources and methods for producing BTX and particularly para-xylene. For example, although steam cracking, or pyrolysis, is the preferred method of producing light olefins (ethylene, propylene, and butenes) from heavier hydrocarbon feedstocks, the process also generates a by-product termed pyrolysis gasoline, steam cracked naphtha (SCN) or pygas. Pygas is a complex mixture of $C_6$ to $C_{10}+$ hydrocarbons that is rich in aromatics, particularly benzene and toluene, but also contains $C_8$, $C_9$, and $C_{10}+$ aromatics. Similarly, catalytic cracking, particularly fluid catalytic cracking (FCC), in addition to producing fuels and light olefins, generates a $C_6$ to $C_{10}$ aromatic rich stream which is similar to pygas and is generally known as cat naphtha. There is significant interest in developing methods of upgrading alternate sources, such as pygas and cat naphtha, to increase the yield of BTX and preferably para-xylene.

For example, U.S. Pat. No. 6,635,792 discloses a process for producing BTX and liquefied petroleum gas (LPG) from a hydrocarbon feedstock having boiling points of 30° C. to 250° C., such as reformate and pyrolysis gasoline. In the process, aromatic components in the hydrocarbon feedstock are converted to BTX-enriched components in the liquid phase through hydrodealkylation and/or transalkylation, and non-aromatic components are converted to LPG-enriched gaseous materials through hydrocracking. The process employs a catalyst comprising platinum/tin or platinum/lead on mordenite, zeolite beta or ZSM-5 and is said to have the advantage of avoiding the need of a solvent extraction step to remove aliphatic compounds from the hydrocarbon feedstock. U.S. Pat. Nos. 7,297,831 and 7,301,063 disclose similar processes.

U.S. Pat. No. 7,176,339 discloses a process for producing xylenes from reformate, which process comprises: (a) providing a reformate containing hydrogen, $C_1$ to $C_5$ hydrocarbons, $C_6$ to $C_7$ hydrocarbons comprising benzene, toluene or mixtures thereof, and $C_8+$ hydrocarbons; (b) removing at least a portion of said hydrogen from said reformate to produce a product containing $C_6$ to $C_7$ hydrocarbons comprising benzene, toluene or mixtures thereof, and $C_8+$ hydrocarbons; and (c) methylating at least a portion of the benzene, toluene, or mixtures thereof present in said product with a methylating agent under vapor phase conditions and in the presence of a catalyst effective for the methylation to produce a resulting product having a higher para-xylene content than the reformate, wherein the catalyst comprises a zeolite-bound-zeolite catalyst and/or a selectivated zeolite and the zeolite comprises ZSM-5. One of the problems alleged to be overcome by this process is the need for an expensive aromatics extraction step to separate $C_6$ to $C_7$ aromatics from the $C_6$ to $C_7$ aliphatics after removal of the hydrogen and $C_1$ to $C_5$ hydrocarbons. A similar process is disclosed in U.S. Pat. No. 7,629,498.

U.S. Pat. No. 7,563,358 discloses a process for producing BTX-enriched product from a hydrocarbon feed comprising: (a) $C_6+$ non-aromatic cyclic hydrocarbons; (b) $C_8+$ single-ring aromatic hydrocarbons having at least one alkyl group containing two or more carbon atoms; and (c) $C_9+$ single-ring aromatic hydrocarbons having at least three methyl groups, by contacting the feed in the presence of hydrogen with a catalyst comprising at least one Group VIII metal and a large or intermediate pore molecular sieve having an alpha value, before incorporation of the Group VIII metal, from about 2 to less than 100 under conditions sufficient for (i) forming aromatic hydrocarbons from $C_6+$ non-aromatic cyclic hydrocarbons; (ii) dealkylating $C_8+$ single-ring aromatic hydrocarbons having at least one alkyl group containing two or more carbon atoms; (iii) transalkylating $C_9+$ single-ring aromatic hydrocarbons having at least three methyl groups; and (iv) disproportionating toluene, to produce a product containing an increased amount of BTX compared to the feed. A preferred hydrocarbon feed is steam cracked naphtha.

U.S. Published Patent Application No. 2009/000988 discloses a process of manufacturing para-xylene, comprising: (a) contacting a pygas feedstock and methylating agent with a catalyst under reaction conditions to produce a product having para-xylene, wherein said product has higher para-xylene content than the para-xylene content of the pygas feedstock; and (f) separating said para-xylene from the product of the step (a), wherein said catalyst comprises a molecular sieve having a Diffusion Parameter for 2,2-dimethylbutane of about 0.1 to 15 sec$^{-1}$ when measured at a temperature of 120° C. and a 2,2-dimethylbutane pressure of 8 kPa-a and said pygas comprises from about 1 wt % to about 65 wt % benzene and from about 5 wt % to 35 wt % toluene.

In U.S. Application Ser. No. 61/421,917 filed Dec. 10, 2010 (and U.S. Ser. No. 13/303,855), we have described a hydrocarbon upgrading process comprising (a) treating a first hydrocarbon stream in at least one of a steam cracker, catalytic cracker, coker, hydrocracker, reformer, and the like, under suitable conditions to produce a second stream comprising $C_6$ to $C_{10}+$ aromatic hydrocarbons; (b) dealkylating and/or transalkylating and/or cracking (D/T/C) the second stream by contact with a suitable catalyst under suitable reaction conditions to produce a third stream having an increased benzene and/or toluene content compared with the second stream and a light paraffin by-product; and (c) methylating at least a portion of the third stream with a methylating agent to selectively produce para-xylene. By integrating different upgrading steps, this process offers significant advantages in terms of higher petrochemical yields and lower energy consumption as compared with existing processes for enriching the BTX content of hydrocarbon streams.

Further investigation into the process described in U.S. Application Ser. No. 61/421,917 (and U.S. Ser. No. 13/303,855) has, however, shown that for hydrocarbon feeds containing large amounts of non-aromatic compounds, the process has challenges of high hydrogen consumption, production of low value products, such as LPG, and potential catalyst aging concerns. In addition, it has been found, contrary to the teaching of the prior art, such as U.S. Pat. Nos. 6,635,792 and 7,176,339, that reduction of the level of non-aromatics to the D/T/C step decreases the hydrogen consumption, reduces LPG made in favor of higher value $C_6$+ raffinate production and reduces aging of the D/T/C catalyst. Surprisingly, introduction of an aliphatics removal step, even though costly, can actually reduce overall investment by decreasing the size of the D/T/C and methylation reactors.

SUMMARY OF THE INVENTION

In one aspect, the invention resides in a hydrocarbon upgrading process comprising:

(a) treating a hydrocarbon feed in at least one of a steam cracker, catalytic cracker, coker, hydrocracker, and reformer under suitable conditions to produce a first stream comprising aliphatic and aromatic hydrocarbons;

(b) recovering from said first stream a second stream composed mainly of $C_6$ to $C_9$ aliphatic and aromatic hydrocarbons;

(c) removing aliphatic hydrocarbons from at least part of the second stream to produce an aliphatic hydrocarbon-depleted stream;

(d) dealkylating and/or transalkylating and/or cracking (D/T/C) said aliphatic hydrocarbon-depleted stream by contact with a catalyst under suitable reaction conditions to produce a third stream having an increased benzene and/or toluene content as compared with said aliphatic hydrocarbon-depleted stream and a light paraffin by-product; and (e) methylating benzene and/or toluene from said third stream with a methylating agent to produce a xylene-enriched stream.

Conveniently, said aliphatic hydrocarbons are removed in (c) by solvent extraction or selective adsorption.

In one embodiment, the second hydrocarbon stream is fractionated, prior to (c), to produce an overhead stream containing $C_7$– hydrocarbons and a bottoms stream containing $C_8$+ hydrocarbons and said aliphatic hydrocarbons are removed from said overhead stream in (c). Conveniently, said bottoms stream is fed to (d).

Conveniently, the catalyst in (d) comprises at least a first and second catalyst compositions, wherein the first catalyst composition comprises a first molecular sieve having a Constraint Index in the range of about 3 to about 12 and at least one metal or compound thereof of Groups 6 to 10 of the Periodic Table of the Elements, and wherein the second catalyst composition comprises a second molecular sieve having a Constraint Index less than 3 and at least one metal or compound thereof of Groups 6 to 10 of the Periodic Table of the Elements.

Conveniently, the first molecular sieve comprises at least one of ZSM-5, ZSM-11, ZSM-22, ZSM-23, ZSM-35, and ZSM-48. Generally, the first molecular sieve has an alpha value in the range of 100 to 1500.

Conveniently, the second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20. Generally, the second molecular sieve has an alpha value in the range of 20 to 500.

In one embodiment, the first molecular sieve is ZSM-5 and the second molecular sieve is ZSM-12. Conveniently, the methylating agent comprises methanol.

Conveniently, the process further comprises recovering para-xylene from said xylene-enriched stream to leave a para-xylene-depleted stream. At least part of said para-xylene-depleted stream may be recycled to (d).

Conveniently, the process further comprises feeding additional benzene to (d). At least part of said additional benzene may be removed from said third stream.

In a further aspect, the invention resides in a hydrocarbon upgrading process comprising:

(a) treating a hydrocarbon feed in at least one of a steam cracker, catalytic cracker, coker, hydrocracker, and reformer under suitable conditions to produce a first stream comprising olefinic and aromatic hydrocarbons;

(b) recovering from said first stream a second stream composed mainly $C_6$ to $C_9$ aliphatic and aromatic hydrocarbons;

(c) separating at least part of the second stream into an overhead stream containing $C_7$– hydrocarbons and a bottoms stream containing $C_8$+ hydrocarbons;

(d) removing aliphatic hydrocarbons from said overhead stream to produce an aliphatic hydrocarbon-depleted $C_7$– stream;

(e) feeding said aliphatic hydrocarbon-depleted $C_7$– stream and said bottoms stream together with hydrogen to a first reaction zone;

(f) contacting the feed to the first reaction zone with a catalyst system effective to dealkylate $C_8$+ single-ring aromatic hydrocarbons having at least one alkyl group containing two or more carbon atoms and transalkylate $C_8$+ single-ring aromatic hydrocarbons having at least two methyl groups and produce a third stream having an increased benzene and/or toluene content compared with said aliphatic hydrocarbon-depleted $C_7$– stream and said bottoms stream; and (g) methylating benzene and/or toluene from said third stream with a methylating agent to produce a xylene-enriched stream.

Conveniently, wherein the first hydrocarbon stream is selected from natural gas liquids, natural gas condensate, naphtha, distillate, gas oils, crude oils, and/or resid.

BRIEF DESCRIPTION OF THE DRAWINGS

FIG. 1 is a schematic drawing of part of a hydrocarbon upgrading process according to one embodiment of the present invention.

DETAILED DESCRIPTION OF THE EMBODIMENTS

The term "$C_n$" hydrocarbon wherein n is a positive integer, e.g., 1, 2, 3, 4, 5, 6, 7, 8, 9, 10, 11, 12, as used herein, means a hydrocarbon having n number of carbon atom(s) per molecule. The term "$C_n$+" hydrocarbon wherein n is a positive integer, e.g., 1, 2, 3, 4, 5, 6, 7, 8, 9, 10, 11, 12, as used herein, means a hydrocarbon having at least n number of carbon atom(s) per molecule. The term "$C_n$–" hydrocarbon wherein n is a positive integer, e.g., 1, 2, 3, 4, 5, 6, 7, 8, 9, 10, 11, 12, as used herein, means a hydrocarbon having no more than n number of carbon atom(s) per molecule.

For the purposes of this invention and the claims thereto, unless otherwise stated, the new numbering scheme for the Periodic Table Groups are used as described in CHEMICAL AND ENGINEERING NEWS, 1985, 63(5), pg. 27.

As used herein "resid" refers to the complex mixture of heavy petroleum compounds otherwise known in the art as residuum or residual. Atmospheric resid is the bottoms product produced in atmospheric distillation where the endpoint of the heaviest distilled product is nominally 650° F. (343° C.), and is referred to as 650° F.+ (343° C.+) resid. Vacuum resid is the bottoms product from a column under vacuum where the heaviest distilled product is nominally 1050° F. (566° C.), and is referred to as 1050° F.+ (566° C.+) resid. (The term "nominally" means here that reasonable experts may disagree on the exact cut point for these terms, but probably by no more than +/−50° F. or at most +/−100° F.) The term "resid" as used herein means the 650° F.+(343° C.+) resid and 1050° F.+(566° C.+) resid unless otherwise specified (note that 650° F.+resid comprises 1050° F.+resid).

Described herein is hydrocarbon upgrading process, in which a hydrocarbon feed is treated in at least one of a steam cracker, catalytic cracker, coker, hydrocracker, and reformer under suitable conditions to produce a first stream enriched in olefinic and/or aromatic hydrocarbons. A second stream composed mainly of $C_6$ to $C_9$ aliphatic and aromatic hydrocarbons is separated from the first stream and at least part of the second stream is then supplied to an extraction unit, where aliphatic hydrocarbons are selectively removed to produce an aromatic hydrocarbon-enriched stream. The aromatic hydrocarbon-enriched stream together with $H_2$ is subsequently fed to a catalytic reactor where the $C_8+$ components of the stream are dealkylated, transalkylated and/or cracked (D/T/C) in the presence of a catalyst to produce a third stream having an increased benzene and/or toluene content compared with said aromatic hydrocarbon-enriched stream and a light paraffin by-product. The light paraffin by-product is recovered and the benzene and/or toluene are separated from the third stream and are methylated typically by reaction with methanol to produce a xylene-enriched product. Preferably said methylation is para-selective meaning that para-xylene is produced at greater than equilibrium ratio with respect to ortho-xylene and meta-xylene.

Hydrocarbon Feedstock

Any hydrocarbon composition conventionally fed to a steam cracker, catalytic cracker, coker, hydrocracker, or reformer can be used as the hydrocarbon feed in the present process. Thus, for example, the hydrocarbon feed can comprise a natural gas liquid or condensate, naphtha, gas oil or any distillate fraction of whole crude oil, including in some cases, the residual fraction remaining after an atmospheric or vacuum distillation process (i.e. resid).

Treating the hydrocarbon feed in the steam cracker, catalytic cracker, coker, hydrocracker, or reformer produces a first hydrocarbon stream having a broad spectrum of olefinic and aromatic hydrocarbons depending on the initial composition of the hydrocarbon feed and also on the unit used to process the feed. The first hydrocarbon stream is then subjected to one or more separation operations to recover $C_3-$ olefins, such as ethylene and propylene, fuel gas and $C_{10}+$ hydrocarbons and leave a second hydrocarbon stream composed mainly $C_6$ to $C_9$ aliphatic and aromatic hydrocarbons. Again, the precise composition of the second hydrocarbon stream will depend on the initial composition of the hydrocarbon feed and on the unit used to process the feed. In fact, depending on the operating targets and efficiency of the fractionation steps used to remove these components, the second hydrocarbon stream may contain quantities (generally less than 20 wt %) of $C_5-$ and $C_{10}+$ hydrocarbons.

In one preferred embodiment, in which a steam cracker is employed as the process unit, the second hydrocarbon stream is a pyrolysis gasoline containing from about 15 wt % to about 65 wt % benzene, from about 5 wt % to about 35 wt % toluene, from about 1 wt % to about 15 wt % of $C_8+$ aromatic compounds and up to 50 wt %, typically about 1 wt % to about 15 wt %, non-aromatics depending on the composition of feedstock to the steam cracker, the intensity of the pyrolysis reaction, and the separation and processing scheme for the pygas stream. Generally, as the intensity of the pyrolysis reaction increases, which can be noted by the rising outlet temperature of the reactor or by the changing of the ratio of two products, such as propylene and methane, more aromatics will be present in the effluent. Similarly, as weight of the feedstock to the pyrolysis furnace increases, the yield of aromatics in the pygas will also increase. Naphthas and gas-oils are conventional feedstocks to steam crackers, including virgin and hydrotreated streams. Resid-containing feeds (considerable portion of 1050° F.+) can be processed by first passing through the convection section of the steam cracking furnace, then passing to a vapor/liquid separating drum, which can optionally be integrated with the pyrolysis furnace, to drop out the heaviest fraction.

Aliphatics Extraction

In the present process, part or all of the second hydrocarbon stream undergoes an initial aliphatics extraction step. Although this requires the addition of a costly aliphatics extraction unit, it has surprisingly been found that the resultant reduction in the level of aliphatics in the feed to the D/T/C and other downstream process units allows the overall capital cost of the system to be reduced.

The entire second hydrocarbon stream can be fed to the aliphatics extraction step. However, since the $C_8+$ portion of the stream typically has a lower non-aromatics content, it is preferable to subject the second hydrocarbon stream to a fractionation step to remove the $C_7-$ hydrocarbons. The $C_7-$ overhead fraction is then passed to the aliphatics extraction step and the $C_8+$ bottoms fraction is fed directly to the D/T/C reactor. Similarly, in some embodiments, the second hydrocarbon stream is subjected to hydrotreating, for example with a cobalt/molybdenum catalyst, to reduce the content of olefins, diolefins, and acetylenes in the second stream prior to aliphatics extraction step.

Reduction of the aliphatic content of the second hydrocarbon stream or the $C_7-$ fraction thereof can be effected by any known process and especially by solvent extraction or selective adsorption. The product of the aliphatics extraction step is an aliphatic hydrocarbon-depleted stream which, as used herein, is intended to mean a hydrocarbon stream containing less than 20 wt %, such as less than 10 wt %, for example less than 5 wt %, even less than 1 wt % of aliphatic hydrocarbons. The aliphatic hydrocarbons removed by the aliphatics extraction step can then be recycled to a steam cracker, or more preferably are recovered as a product, for example, for use as a gasoline blending stock.

The entire aliphatic hydrocarbon-depleted product remaining after removal of the aliphatic component can then be fed to the D/T/C reactor but generally the product is initially passed to a distillation system where at least a toluene-containing fraction is removed from the product and fed to the methylation reactor. In some cases, a benzene-containing fraction is also removed by the distillation system and can be recovered as a product of the process or fed to the methylation reactor together with the toluene-containing fraction.

Thus the feed to the D/T/C reactor is mainly benzene, $C_8$ aromatics and $C_9$ aromatics. Hydrogen is also supplied to the D/T/C reactor.

Dealkylation, Transalkylation and Cracking

Although a single catalyst can be used in the D/T/C reactor, generally the reactor includes a plurality of different catalyst compositions.

In particular, the D/T/C catalyst system typically includes a first catalyst composition comprising a first molecular sieve having a Constraint Index in the range of about 3 to about 12 and at least one metal or compound thereof from Groups 6 to 12 of the Periodic Table of the Elements.

Constraint Index is a convenient measure of the extent to which an aluminosilicate or other molecular sieve provides controlled access to molecules of varying sizes to its internal structure. For example, molecular sieves which provide a highly restricted access to and egress from its internal structure have a high value for the Constraint Index. Molecular sieves of this kind usually have pores of small diameter, e.g., less than 5 Angstroms. On the other hand, molecular sieves which provide relatively free access to their internal pore structure have a low value for the Constraint Index, and usually pores of large size. The method by which Constraint Index is determined is described fully in U.S. Pat. No. 4,016,218, which is incorporated herein by reference for the details of the method including that Constraint Index is determined on the zeolite alone without any treatment to adjust the diffusivity of the catalyst.

Suitable molecular sieves for use in the first catalyst composition comprise at least one of ZSM-5, ZSM-11, ZSM-22, ZSM-23, ZSM-35, ZSM-48, ZSM-57 and ZSM-58. ZSM-5 is described in detail in U.S. Pat. No. 3,702,886 and Re. 29,948. ZSM-11 is described in detail in U.S. Pat. No 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is more particularly described in U.S. Pat. Nos. 4,234,231 and 4,375,573. ZSM-57 is described in U.S. Pat. No. 4,873,067. ZSM-58 is described in U.S. Pat. No. 4,698,217.

In one preferred embodiment, the first molecular sieve comprises ZSM-5 and especially ZSM-5 having an average crystal size of less than 0.1 micron, such as about 0.05 micron.

Conveniently, the first molecular sieve has an alpha value in the range of about 100 to about 1500, such as about 150 to about 1000, for example about 300 to about 600. Alpha value is a measure of the cracking activity of a catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, page 395.

Generally, the first molecular sieve is an aluminosilicate having a silica to alumina molar ratio of less than 1000, typically from about 10 to about 100.

Typically, the first catalyst composition comprises at least 1 wt %, preferably at least 10 wt %, more preferably at least 50 wt %, of the first molecular sieve.

In addition to a molecular sieve having a Constraint Index in the range of about 3 to about 12, the first catalyst composition comprises at least a first metal, and generally first and second different metals, or compounds thereof of Groups 6 to 12 of the Periodic Table of the Elements.

The first metal is generally selected from platinum, palladium, iridium, rhenium and mixtures thereof, whereas the second metal, if present, is chosen so as to lower the benzene saturation activity of the first metal and is conveniently selected from at least one of copper, silver, gold, ruthenium, iron, tungsten, molybdenum, cobalt, nickel, tin, and zinc. In one embodiment, the first metal comprises platinum and said second metal comprises copper.

Conveniently, the first metal is present in the first catalyst in amount between about 0.01 wt % and about 5 wt % of the first catalyst and the optional second metal is present in the first catalyst in amount between about 0.01 wt % and about 1 wt % of the first catalyst.

In most cases, the first catalyst composition also comprises a binder or matrix material that is resistant to the temperatures and other conditions employed in the D/T/C reactor. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may include, for example, naturally occurring clays, e.g., bentonite and kaolin, to improve the crush strength of the catalyst composition under commercial operating conditions.

Naturally occurring clays that can be composited with the first molecular sieve as a binder for the first catalyst composition include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the first molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia. It may also be advantageous to provide at least a part of the foregoing porous matrix binder material in colloidal form so as to facilitate extrusion of the catalyst composition.

Typically the first molecular sieve is admixed with the binder or matrix material so that the first catalyst composition contains the binder or matrix material in an amount ranging from 5 wt % to 95 wt %, and typically from 10 wt % to 60 wt %.

The first catalyst bed composition is effective to dealkylate $C_8$+ single-ring aromatic hydrocarbons having at least one alkyl group containing two or more carbon atoms in the D/T/C feed. Thus exemplary reactions proceeding in the presence of the first catalyst composition are cracking of ethyltoluene, ethylxylene and cumene to toluene, xylene and benzene respectively. The cracking is of course accompanied by production of ethylene and propylene but these are immediately hydrogenated to the corresponding alkanes.

Generally, the D/T/C catalyst system also includes a second catalyst composition comprising a second molecular sieve having a Constraint Index less than 3 and optionally one or more metals or compounds thereof of Groups 6 to 12 of the Periodic Table of the Elements.

Suitable molecular sieves for use in the second catalyst composition comprise at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, PSH-3, SSZ-25, MCM-36, MCM-49, MCM-56, EMM-10, EMM-10-P and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. MCM-22 is described in U.S. Pat. No. 4,954,325. PSH-3 is described in U.S. Pat. No. 4,439,409. SSZ-25 is described in U.S. Pat. No. 4,826,667. MCM-36 is described in U.S. Pat. No. 5,250,277. MCM-49 is described in U.S. Pat. No. 5,236,575. MCM-56 is described in U.S. Pat. No. 5,362,697.

In one preferred embodiment, the second molecular sieve comprises ZSM-12 and especially ZSM-12 having an average crystal size of less than 0.1 micron, such as about 0.05 micron.

Conveniently, the second molecular sieve has an alpha value of at least 20, such as from about 20 to about 500, for example from about 30 to about 100.

Generally, the second molecular sieve is an aluminosilicate having a silica to alumina molar ratio of less than 500, typically from about 50 to about 300.

Typically, the second catalyst composition comprises at least 1 wt %, preferably at least 10 wt %, more preferably at least 50 wt %, and most preferably at least 65 wt %, of the second molecular sieve.

Optionally, the second catalyst composition comprises at least one and preferably at least two metals or compounds thereof of Groups 6 to 12 of the Periodic Table of the Elements. Generally, the second catalyst composition comprises the same first and second metals present in the same amounts as contained by the first catalyst composition.

Generally, the second catalyst composition also contains a binder or matrix material, which can be any of the materials listed as being suitable for the first catalyst and can be present in an amount ranging from 5 wt % to 95 wt %, and typically from 10 wt % to 60 wt %, of the second catalyst composition.

Conveniently, the weight ratio of the first catalyst composition to the second catalyst composition is typically in the range of 5:95 to 75:25.

The second catalyst composition is effective to transalkylate $C_9+$ single-ring aromatic hydrocarbons having at least three methyl groups in the D/T/C feed. Thus an exemplary reaction proceeding in the presence of the second catalyst composition is transalkylation of xylene with benzene to produce two molecules of toluene.

Optionally, the D/T/C catalyst system includes a third catalyst composition comprising a third molecular sieve having a Constraint Index from about 1 to 12. Suitable molecular sieves for use in the third catalyst comprise at least one of ZSM-5, ZSM-11, ZSM-12, zeolite beta, ZSM-22, ZSM-23, ZSM-35, ZSM-48, ZSM-57, and ZSM-58, with ZSM-5 being preferred.

Generally, the third catalyst composition also contains a binder or matrix material, which can be any of the materials listed as being suitable for the first catalyst and can be present in an amount ranging from 5 wt % to 95 wt %, and typically from 10 wt % to 60 wt %, of the third catalyst composition.

The third catalyst composition is effective to crack non-aromatic cyclic hydrocarbons in the effluent from the first and second catalyst beds. In particular, the third catalyst composition is effective to crack benzene co-boilers, such as cyclohexane, so as to facilitate the recovery of a high purity benzene product from the D/T/C effluent.

In a first embodiment, the D/T/C catalyst system comprises (a) a first catalyst composition comprising a 50 wt % ZSM-5:50 wt % $Al_2O_3$ extrudate which has been impregnated with 0.115 wt % Pt and steamed to a target alpha value of 350; (b) a second catalyst composition comprising a 65 wt % ZSM-12:35 wt % $Al_2O_3$ extrudate which has been impregnated with 0.1 wt % Pt; and (c) a third catalyst composition comprising a metal-free 65 wt % ZSM-5:35 wt % $Al_2O_3$ extrudate.

In a second embodiment, the D/T/C catalyst system comprises (a) a first catalyst composition comprising a 50 wt % ZSM-5:50 wt % $Al_2O_3$ extrudate which has been impregnated with 0.115 wt % Pt and 0.0375 wt % copper and steamed to a target alpha value of 350; (b) a second catalyst composition comprising a 65 wt % ZSM-12:35 wt % $Al_2O_3$ extrudate which has been impregnated with 0.1 wt % Pt and 0.0326 wt % copper; and (c) a third catalyst composition comprising a metal-free 65 wt % ZSM-5:35 wt % $Al_2O_3$ extrudate.

The various catalyst compositions may be contained within a single bed; mounted within multiple beds in a single reactor, or located within multiple reactor shells.

The product of the D/T/C reactor is a third hydrocarbon stream having an increased molar concentration of benzene and/or toluene as compared with the feed and a $C_3-$ paraffin by-product, which is recovered for use as fuel or sent to a steam cracker as supplemental feed. The third hydrocarbon stream is fed to a distillation system where the stream is divided into at least a toluene-containing fraction is removed from the product and fed to the methylation reactor. In some cases, a benzene-containing fraction is also removed by the distillation system and can be recovered as a product of the process or fed to the methylation reactor together with the toluene-containing fraction.

Benzene and/or Toluene Methylation

The toluene and, where present, benzene removed from the third hydrocarbon stream is fed to a methylation reactor where the aromatic feed is methylated, generally with methanol in the presence of a specific zeolite catalyst at a temperature between about 500° C. and about 700° C., preferably between about 500° C. and about 600° C., a pressure of between about 1 atmosphere and 1000 psig (100 kPa and 7000 kPa), a weight hourly space velocity of between about 0.5 and 1000, and a molar ratio of toluene to methanol (in the reactor charge) of at least about 0.2, e.g., from about 0.2 to about 20. The process is preferably conducted in the presence of added water such that the molar ratio of water to benzene/toluene+methanol in the feed is between about 0.01 and about 10.

The zeolite catalyst employed in the alkylation process is selected to have a Diffusion Parameter for 2,2-dimethylbutane of about 0.1 to 15 $sec^{-1}$, and preferably 0.5 to 10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q, D is the diffusion coefficient (cm$^2$/sec) and r is the crystal radius (cm). Graphical solutions for the plane sheet model are given by J. Crank in "The Mathematics of Diffusion", Oxford University Press, Ely House, London, 1967.

The zeolite employed in the present alkylation process is normally a medium-pore size aluminosilicate zeolite. Medium pore zeolites are generally defined as those having a pore size of about 5 to 7 Angstroms, such that the zeolite freely sorbs molecules such as n-hexane, 3-methylpentane, benzene, and p-xylene. Likewise preferred, medium pore zeolites have a Constraint Index of about 3 to 12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are preferred for the present alkylation process since the size and shape of their pores favor the production of p-xylene over the other xylene isomers. However, conventional forms of these zeolites have Diffusion Parameter values in excess of the 0.1 to 15 sec$^{-1}$ range referred to above. However, the required diffusivity for the catalyst can be achieved by severely steaming the catalyst so as to effect a controlled reduction in the micropore volume of the catalyst to not less than 50%, and preferably 50% to 90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950° C. to about 1075° C., and most preferably about 1000° C. to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, preferably selected from oxides of the elements of Groups IIA, IIIA, IIIB, IVA, IVB, VA, and VIA of the Periodic Table (IUPAC version). Most preferably, said at least one oxide modifier is selected from oxides of boron, magnesium, calcium, lanthanum and most preferably phosphorus. In some cases, it may be desirable to combine the zeolite with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 wt % and about 20 wt %, and preferably is between about 0.1 wt % and about 10 wt %, based on the weight of the final catalyst.

Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 wt % and about 30 wt %. Suitable phosphorus compounds include, but are not limited to, phosphonic, phosphinous, phosphorus and phosphoric acids, salts and esters of such acids and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3 to 5 hours. Similar techniques known in the art can be used to incorporate other modifying oxides into the catalyst employed in the alkylation process.

In addition to the zeolite and modifying oxide, the catalyst employed in the alkylation process may include one or more binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia, and silica-magnesia-zirconia.

The relative proportions of porous crystalline material and inorganic oxide matrix vary widely, with the content of the former ranging from about 1 wt % to about 90 wt % and more usually, particularly when the composite is prepared in the form of beads, in the range of about 2 wt % to about 80 wt % of the composite. Preferably, the matrix material comprises silica or a kaolin clay.

The alkylation catalyst used in the present process may optionally be precoked. The precoking step is preferably carried out by initially utilizing the uncoked catalyst in the toluene methylation reaction, during which coke is deposited on the catalyst surface and thereafter controlled within a desired range, typically from about 1 wt % to about 20 wt % and preferably from about 1 wt % to about 5 wt %, by periodic regeneration by exposure to an oxygen-containing atmosphere at an elevated temperature.

One of the advantages of the catalyst described herein is its ease of regenerability. Thus, after the catalyst accumulates coke as it catalyzes the toluene methylation reaction, it can easily be regenerated by burning off a controlled amount of coke in a partial combustion atmosphere in a regenerator at temperatures in the range of from about 400° C. to about 700° C. The coke loading on the catalyst may thereby be reduced or substantially eliminated in the regenerator. If it is desired to maintain a given degree of coke loading, the regeneration step may be controlled such that the regenerated catalyst returning to the toluene methylation reaction zone is coke-loaded at the desired level.

The present process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

Using the present process, toluene can be alkylated with methanol so as to produce para-xylene at a selectivity of at least about 80 wt % (based on total $C_8$ aromatic product) at a per-pass toluene conversion of at least about 15 wt % and a trimethylbenzene production level less than 1 wt %. The olefin-rich light gas by-product may be recovered in a dedicated olefins recovery unit or routed to a steam cracker olefins recovery section. Unreacted toluene, methanol and a portion of the water product may be recycled to the methylation reactor and heavy byproducts routed to fuels dispositions. The $C_8$ fraction is routed to a para-xylene recovery unit, which typically operates by fractional crystallization or by selective adsorption (e.g., Parex or Eluxyl) to recover a para-xylene product stream from the alkylation effluent and leave a para-xylene-depleted stream containing mainly $C_7$ and $C_8$ hydrocarbons. The para-xylene-depleted stream is conveniently recycled to the D/T/C reactor, generally after removal of any toluene for recycle to methylation step. Alternatively, the para-xylene-depleted stream may be isomerized and recycled to the para-xylene recovery unit.

The invention will now be more particularly described with reference to the accompanying drawing and the following non-limiting Examples.

Referring initially to FIG. 1, a $C_6$ to $C_9$ aliphatic and aromatic hydrocarbon product from a steam cracker (not shown) is fed by line 11 to a first fractionation system 12, where the product is separated into an overhead stream containing $C_7-$ hydrocarbons and a bottoms stream containing $C_8+$ hydrocarbons. The $C_7-$ overhead stream is then fed by line 13 to a solvent extraction unit 14, while the $C_8+$ bottoms stream is fed by line 15 to a D/T/C reactor 16.

The solvent extraction unit 14 removes aliphatic hydrocarbons from the $C_7-$ overhead stream to leave an aliphatic hydrocarbon-depleted stream which is fed by line 17 to a second fractionation system 18. The aliphatic hydrocarbons removed by the extraction unit 14 are recovered and fed by line 36 either for recycle to the steam cracker or for use as a gasoline blending stock.

The second fractionation system 18 also receives the $C_6+$ product stream from the D/T/C reactor 16 and a para-xylene-depleted effluent stream from a methylation reactor 19. The second fractionation system 18 divides these various hydrocarbon streams into a benzene-rich stream in first overhead line 21, a toluene-rich steam in second overhead line 22, a $C_8$ and $C_9$-rich steam in first bottoms line 23 and a $C_{10}+$-rich stream in second bottoms line 24.

The toluene-rich steam in second overhead line 22 and part of the benzene-rich stream in first overhead line 21 are fed together with methanol in line 25 to the methylation reactor 19 where the benzene and toluene are converted to xylenes. The xylene-enriched effluent stream from the methylation reactor 19 is then fed by line 26 to a para-xylene recovery unit 27, where a para-xylene product stream is recovered in line 28, to leave a para-xylene-depleted stream which is recycled to the second fractionation system 18 via line 29. The methylation reactor 19 also produces an olefin-rich light gas, which is recovered by line 31 and can be combined with the light olefins produced in the steam cracker.

The $C_8$ and $C_9$-rich steam in first bottoms line 23 is fed with the $C_8+$ bottoms stream in line 15 to the D/T/C reactor 16, which also receives part of the benzene-rich stream in first overhead line 21 via slipstream 32 and also receives make-up hydrogen via line 33. The D/T/C reactor 16 converts the various $C_8$ and $C_9$ hydrocarbons in the lines 15 and 23 to a product enriched in benzene and/or toluene and a light paraffin by-product. The benzene and/or toluene-enriched product is recycled by line 34 to the second fractionation system 18, whereas the light paraffin by-product is recovered in line 35 for use as a fuel.

In another embodiment, this invention relates to:

1. A hydrocarbon upgrading process comprising:
    (a) treating a hydrocarbon feed in at least one of a steam cracker, catalytic cracker, coker, hydrocracker, and reformer under suitable conditions to produce a first stream comprising aliphatic and aromatic hydrocarbons;
    (b) recovering from said first stream a second stream composed mainly of $C_6$ to $C_9$ aliphatic and aromatic hydrocarbons;
    (c) removing aliphatic hydrocarbons from at least part of the second stream to produce an aliphatic hydrocarbon-depleted stream;
    (d) dealkylating and/or transalkylating and/or cracking (D/T/C) said aliphatic hydrocarbon-depleted stream by contact with a catalyst under suitable reaction conditions to produce a third stream having an increased benzene and/or toluene content as compared with said aliphatic hydrocarbon-depleted stream and a light paraffin by-product; and
    (e) methylating benzene and/or toluene from said third stream with a methylating agent to produce a xylene-enriched stream.

2. The process of paragraph 1, wherein said aliphatic hydrocarbons are separated in (c) by solvent extraction or selective adsorption.

3. The process of paragraph 1 or 2, wherein the second hydrocarbon stream is fractionated, prior to (c), to produce an overhead stream containing $C_7-$ hydrocarbons and a bottoms stream containing $C_8+$ hydrocarbons and said aliphatic hydrocarbons are removed from said overhead stream in (c).

4. The process of paragraph 3, wherein said bottoms stream is also fed to (d).

5. The process of paragraph 1, 2, 3 or 4, wherein the second stream is hydrotreated to reduce the content of olefins, diolefins, and acetylenes prior to (c).

6. The process of any of paragraphs 1 to 5, wherein the catalyst in (d) comprises at least a first and second catalyst composition, wherein the first catalyst composition comprising a first molecular sieve having a Constraint Index in the range of about 3 to about 12 and at least one metal or compound thereof of Groups 6 to 10 of the Periodic Table of the Elements, and wherein the second catalyst composition comprising a second molecular sieve having a Constraint Index less than 3 and at least one metal or compound thereof of Groups 6 to 10 of the Periodic Table of the Elements.

7. The process of paragraph 6, wherein said first molecular sieve comprises at least one of ZSM-5, ZSM-11, ZSM-22, ZSM-23, ZSM-35, and ZSM-48.

8. The process of paragraph 6 or 7, wherein said first molecular sieve has an alpha value in the range of 100 to 1500.

9. The process of paragraph 6, 7, or 8, wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20.

10. The process of paragraph 6, 7, 8, or 9 wherein said second molecular sieve has an alpha value in the range of 20 to 500.

11. The process of paragraph 6, wherein said first molecular sieve is ZSM-5 and said second molecular sieve is ZSM-12.

12. The process of any of paragraphs 1 to 11, wherein said methylating agent comprises methanol.

13. The process of any of paragraphs 1 to 12, wherein said methylating of benzene and/or toluene is para-selective.

14. The process of any of paragraphs 1 to 13, further comprising recovering para-xylene from said xylene-enriched stream to leave a para-xylene-depleted stream.

15. The process of paragraph 14, further comprising recycling at least part of said para-xylene-depleted stream to (d).

16. The process of any of paragraphs 1 to 15, further comprising feeding additional benzene to (d).

17. The process of paragraph 16, wherein at least part of said additional benzene is removed from said third stream.

18. The process of any of paragraphs 1 to 17, wherein the hydrocarbon feed is selected from natural gas liquids, natural gas condensate, naphtha, distillate, gas oils, crude oils, and/or resid.

19. A hydrocarbon upgrading process comprising:
(a) treating a hydrocarbon feed in at least one of a steam cracker, catalytic cracker, coker, hydrocracker, and reformer under suitable conditions to produce a first stream comprising aliphatic and aromatic hydrocarbons;
(b) recovering from said first stream a second stream composed mainly of $C_6$ to $C_9$ aliphatic and aromatic hydrocarbons;
(c) separating at least part of the second stream into a overhead stream containing $C_7-$ hydrocarbons and a bottoms stream containing $C_8+$ hydrocarbons;
(d) removing aliphatic hydrocarbons from said overhead stream to produce an aliphatic hydrocarbon-depleted $C_7-$ stream;
(e) feeding said aliphatic hydrocarbon-depleted $C_7-$ stream and said bottoms stream together with hydrogen to a first reaction zone;
(f) contacting the feed to the first reaction zone with a catalyst system effective to dealkylate $C_8+$ single-ring aromatic hydrocarbons having at least one alkyl group containing two or more carbon atoms and transalkylate $C_8+$ single-ring aromatic hydrocarbons having at least two methyl groups and produce a third stream having an increased benzene and/or toluene content compared with said aliphatic hydrocarbon-depleted $C_7-$ stream and said bottoms stream; and
(g) methylating benzene and/or toluene from said third stream with a methylating agent to produce a xylene-enriched stream.

20. The process of paragraph 19, further comprising hydrotreating the second stream before the said separating (c).

21. The process of paragraph 19 or 20, wherein said aliphatic hydrocarbons are separated in (d) by solvent extraction or selective adsorption.

22. The process of paragraph 19, 20, or 21 wherein the second stream is hydrotreated to reduce the content of olefins, diolefins, and acetylenes prior to (d).

23. The process of any of paragraphs 19 to 22, wherein the catalyst in (f) comprises at least a first and second catalyst composition, wherein the first catalyst composition comprising a first molecular sieve having a Constraint Index in the range of about 3 to about 12 and at least one metal or compound thereof of Groups 6 to 10 of the Periodic Table of the Elements, and wherein the second catalyst composition comprising a second molecular sieve having a Constraint Index less than 3 and at least one metal or compound thereof of Groups 6 to 10 of the Periodic Table of the Elements.

24. The process of paragraph 23, wherein said first molecular sieve comprises at least one of ZSM-5, ZSM-11, ZSM-22, ZSM-23, ZSM-35, and ZSM-48.

25. The process of paragraph 23 or 24, wherein said first molecular sieve has an alpha value in the range of 100 to 1500.

26. The process of paragraph 23, 24 or 25 wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20.

27. The process of paragraph 23, 24, 25 or 26, wherein said second molecular sieve has an alpha value in the range of 20 to 500.

28. The process of paragraph 23, wherein said first molecular sieve is ZSM-5 and said second molecular sieve is ZSM-12.

29. The process of any of paragraphs 19 to 28, wherein said methylating agent is methanol.

30. The process of any of paragraphs 19 to 29, further including (h) recovering para-xylene from said xylene-enriched stream.

31. The process of any of paragraphs 19 to 30, wherein the hydrocarbon feed is selected from natural gas liquids, natural gas condensate, naphtha, distillate, gas oils, crude oils, and/or resid.

32. The process of any of paragraphs 19 to 31, wherein said aliphatic hydrocarbons removed in (d) are recovered for use as a gasoline blending component.

33. The process of any of paragraphs 19 to 32, wherein said methylating of benzene and/or toluene is para-selective.

Example 1 (Comparative)

Table 1 provides the estimated aromatics material balance for a hydrocarbon upgrading process as described in our co-pending U.S. application Ser. No. 13/303,855, filed Nov. 23, 2011 (which claims the benefit of and priority to U.S. Ser. No. 61/421,917 filed Dec. 10, 2010), in which the entire $C_6$ to $C_9$ aliphatic and aromatic hydrocarbon feed from the steam cracker is fed to the D/T/C reactor without removal of the C$_7$– aliphatic component. All amounts specified in Table 1 are in kilotons per annum (kTa).

Example 2

Table 2 provides the estimated aromatics material balance for a hydrocarbon upgrading process as described in Example 1 but with extraction of the C$_7$– aliphatic component before the D/T/C step.

Comparing Tables 1 and 2, it will be seen, using the same amount of feed from the steam cracker, the process of Example 1 required 45.5 kTa of make-up hydrogen and produced 133.5 kTa of low value LPG, with the hydrogen purge being 167.2 kTa. In contrast, the process of Example 2 required only 23.3 kTa of make-up hydrogen and produced only 86.7 kTa of low value LPG and 244.2 kTa of higher value C$_7$– aliphatics, with the hydrogen purge being only 54.7 kTa. In addition, the process of Example 2 produced 626.5 kTa of para-xylene product as compared with only 617.4 kTa in Example 1.

TABLE 1

SCN Upgrading - Aromatics Material Balance (kTa) - BASE CASE

| | Inputs | | | | Outputs | | | | | MTAM | | | |
| | | | | | | A10+ (TP) | | | | Off-gas | Heavies | | |
| Components | SCN feed | MeOH | TP H2 | Total | PX product | to fuel oil (T-103 btms) | TP off-gas to SC feed | TP H2 purge | Coke | to SC recovery | to fuel oil | Water | Total |
|---|---|---|---|---|---|---|---|---|---|---|---|---|---|
| Inputs | | | | | | | | | | | | | |
| Benzene | 186.03 | 0.00 | 0.00 | 186.03 | | | | | | | | | |
| C6NAs | 127.19 | 0.00 | 0.00 | 127.19 | | | | | | | | | |
| Toluene | 144.18 | 0.00 | 0.00 | 144.18 | | | | | | | | | |
| C7 NAs | 81.82 | 0.00 | 0.00 | 81.82 | | | | | | | | | |
| EB | 63.53 | 0.00 | 0.00 | 63.53 | | | | | | | | | |
| Xylenes | 72.32 | 0.00 | 0.00 | 72.32 | | | | | | | | | |
| C8NAs | 41.73 | 0.00 | 0.00 | 41.73 | | | | | | | | | |
| C9+ (A9/A10s) | 236.08 | 0.00 | 0.00 | 236.08 | | | | | | | | | |
| Hydrogen | 0.00 | 0.00 | 28.44 | 28.44 | | | | | | | | | |
| C1-C5 in TP H2 | 0.00 | 0.00 | 17.04 | 17.04 | | | | | | | | | |
| MeOH | 0.00 | 413.83 | 0.00 | 413.83 | | | | | | | | | |
| Outputs | | | | | | | | | | | | | |
| Paraxylene | | | | | 617.40 | 1.55 | 0.55 | 0.33 | 0.00 | 0.00 | 0.00 | 0.00 | 619.84 |
| Hydrogen | | | | | 0.00 | 0.00 | 0.20 | 15.49 | 0.00 | 0.00 | 0.00 | 0.00 | 15.70 |
| Carbon Monoxide | | | | | 0.00 | 0.00 | 0.00 | 0.00 | 0.00 | 3.45 | 0.00 | 0.00 | 3.45 |
| Methane | | | | | 0.00 | 0.00 | 1.50 | 15.92 | 0.00 | 21.23 | 0.00 | 0.00 | 38.64 |
| Ethane | | | | | 0.00 | 0.00 | 44.38 | 90.06 | 0.00 | 7.84 | 0.00 | 0.00 | 142.28 |
| Ethylene | | | | | 0.00 | 0.00 | 0.00 | 0.00 | 0.00 | 32.45 | 0.00 | 0.00 | 32.45 |
| Propane | | | | | 0.00 | 0.00 | 47.61 | 32.73 | 0.00 | 3.52 | 0.00 | 0.00 | 83.86 |
| Propylene | | | | | 0.00 | 0.00 | 0.00 | 0.00 | 0.00 | 33.00 | 0.00 | 0.00 | 33.00 |
| Butene-1 | | | | | 0.00 | 0.00 | 0.00 | 0.00 | 0.00 | 5.70 | 0.00 | 0.00 | 5.70 |
| Butene-2 | | | | | 0.00 | 0.00 | 0.00 | 0.00 | 0.00 | 13.29 | 0.00 | 0.00 | 13.29 |
| Isobutylene | | | | | 0.00 | 0.00 | 0.00 | 0.00 | 0.00 | 4.75 | 0.00 | 0.00 | 4.75 |
| C5 olefins | | | | | 0.00 | 0.00 | 0.00 | 0.00 | 0.00 | 9.50 | 0.00 | 0.00 | 9.50 |
| C4-C6 Offgas | | | | | 0.00 | 0.00 | 31.59 | 8.68 | 0.00 | 8.37 | 0.00 | 0.00 | 48.64 |
| BZ + Tol in Offgas | | | | | 0.00 | 0.00 | 6.51 | 3.92 | 0.00 | 0.00 | 0.00 | 0.00 | 10.44 |
| C9+ to fuel oil | | | | | 0.00 | 78.35 | 1.14 | 0.01 | 0.00 | 0.00 | 24.28 | 0.00 | 103.78 |
| Wastewater | | | | | 0.00 | 0.00 | 0.00 | 0.00 | 0.00 | 0.00 | 0.00 | 230.45 | 230.45 |
| Coke | | | | | 0.00 | 0.00 | 0.00 | 0.00 | 16.79 | 0.00 | 0.00 | 0.00 | 16.79 |
| Total | 952.9 | 413.8 | 45.5 | 1,412.2 | 617.4 | 79.9 | 133.5 | 167.2 | 16.8 | 143.1 | 24.3 | 230.5 | 1,412.6 |
| Fraction of SCN feed | 1.00 | 0.43 | 0.05 | | 0.65 | 0.08 | 0.14 | 0.18 | 0.02 | 0.15 | 0.03 | 0.24 | |

TABLE 2

SCN Upgrading (w/B/T Extraction) - Aromatics Material Balance (kTa)

| | Inputs | | | | Outputs | | | | | | | | | |
|---|---|---|---|---|---|---|---|---|---|---|---|---|---|---|
| Components | SCN feed | MeOH | TP H2 | Total | PX product | A10+ (TP) to fuel oil (T-103 btms) | TP off-gas to SC feed | TP H2 purge | Extraction Raffinate | Coke | MTAM Off-gas to SC recovery | MTAM Heavies to fuel oil | Water | Total |
| Inputs | | | | | | | | | | | | | | |
| Benzene | 186.03 | 0.00 | 0.00 | 186.03 | | | | | | | | | | |
| C6NAs | 127.19 | 0.00 | 0.00 | 127.19 | | | | | | | | | | |
| Toluene | 144.18 | 0.00 | 0.00 | 144.18 | | | | | | | | | | |
| C7 NAs | 81.82 | 0.00 | 0.00 | 81.82 | | | | | | | | | | |
| EB | 63.53 | 0.00 | 0.00 | 63.53 | | | | | | | | | | |
| Xylenes | 72.32 | 0.00 | 0.00 | 72.32 | | | | | | | | | | |
| C8NAs | 41.73 | 0.00 | 0.00 | 41.73 | | | | | | | | | | |
| C9+ (A9/A10s) | 236.08 | 0.00 | 0.00 | 236.08 | | | | | | | | | | |
| Hydrogen | 0.00 | 0.00 | 14.57 | 14.57 | | | | | | | | | | |
| C1-C5 in TP H2 | 0.00 | 0.00 | 8.73 | 8.73 | | | | | | | | | | |
| MeOH | 0.00 | 429.00 | 0.00 | 429.00 | | | | | | | | | | |
| Outputs | | | | | | | | | | | | | | |
| Paraxylene | | | | | 626.47 | 2.07 | 0.36 | 0.13 | 0.01 | 0.00 | 0.00 | 0.00 | 0.00 | 629.05 |
| Hydrogen | | | | | 0.00 | 0.00 | 0.19 | 7.05 | 0.00 | 0.00 | 0.00 | 0.00 | 0.00 | 7.24 |
| Carbon Monoxide | | | | | 0.00 | 0.00 | 0.00 | 0.00 | 0.00 | 0.00 | 3.58 | 0.00 | 0.00 | 3.58 |
| Methane | | | | | 0.00 | 0.00 | 1.68 | 7.43 | 0.00 | 0.00 | 10.56 | 0.00 | 0.00 | 19.67 |
| Ethane | | | | | 0.00 | 0.00 | 31.54 | 26.12 | 0.00 | 0.00 | 1.38 | 0.00 | 0.00 | 59.03 |
| Ethylene | | | | | 0.00 | 0.00 | 0.00 | 0.00 | 0.00 | 0.00 | 21.82 | 0.00 | 0.00 | 21.82 |
| Propane | | | | | 0.00 | 0.00 | 41.36 | 11.58 | 0.00 | 0.00 | 0.49 | 0.00 | 0.00 | 53.43 |
| Propylene | | | | | 0.00 | 0.00 | 0.00 | 0.00 | 0.00 | 0.00 | 5.43 | 0.00 | 0.00 | 5.43 |
| Butene-1 | | | | | 0.00 | 0.00 | 0.00 | 0.00 | 0.00 | 0.00 | 0.49 | 0.00 | 0.00 | 0.49 |
| Butene-2 | | | | | 0.00 | 0.00 | 0.00 | 0.00 | 0.00 | 0.00 | 1.15 | 0.00 | 0.00 | 1.15 |
| Iso-butylene | | | | | 0.00 | 0.00 | 0.00 | 0.00 | 0.00 | 0.00 | 0.41 | 0.00 | 0.00 | 0.41 |
| C5 olefins | | | | | 0.00 | 0.00 | 0.00 | 0.00 | 0.00 | 0.00 | 0.18 | 0.00 | 0.00 | 0.18 |
| C4-C7 Offgas/Raffinate | | | | | 0.00 | 0.00 | 6.47 | 0.97 | 240.53 | 0.00 | 3.13 | 0.00 | 0.00 | 251.10 |
| BZ + Tol in Offgas | | | | | 0.00 | 0.00 | 3.97 | 1.44 | 4.58 | 0.00 | 0.00 | 0.00 | 0.00 | 9.99 |
| C9+ to fuel oil | | | | | 0.00 | 66.73 | 1.09 | 0.00 | 0.22 | 0.00 | 0.00 | 24.98 | 0.00 | 93.02 |
| Wastewater | | | | | 0.00 | 0.00 | 0.00 | 0.00 | 0.00 | 0.00 | 0.00 | 0.00 | 238.90 | 238.90 |
| Coke | | | | | 0.00 | 0.00 | 0.00 | 0.00 | 0.00 | 10.79 | 0.00 | 0.00 | 0.00 | 10.69 |
| Total | 952.9 | 429.0 | 23.3 | 1,405.2 | 626..5 | 68.8 | 86.7 | 54.7 | 245.3 | 10.7 | 48.6 | 25.0 | 238.9 | 1,405.2 |
| Total Base Case | 952.9 | 413.8 | 45.5 | 1,412.2 | 617.4 | 79.9 | 133.5 | 167.2 | 0.00 | 16.8 | 143.1 | 24.3 | 230.5 | 1,412.6 |
| Delta (kTa) | 0.0 | 15.2 | −22.2 | −7.0 | 9.1 | −11.1 | −46.8 | −112.4 | 245.3 | −6.1 | −94.5 | 0.7 | 8.4 | −7.4 |
| Delta (%) | 0% | 4% | −49% | 0% | 1% | −14% | −35% | −67% | 0% | −36% | −66% | 3% | 4% | −1% |

Example 3

Example 3 provides the results of conducting the D/T/C reaction on two different feeds, one being substantially entirely aromatic and the other containing 83.6 wt % aromatics and 16.4 wt % non-aromatics. In each case, the reaction was conducting using 30 gm of a dual bed catalyst composed of (a) 90 wt % of a first catalyst comprising a 50 wt % ZSM-5:50 wt % $Al_2O_3$ extrudate impregnated with 0.115 wt % Pt and steamed to a target alpha value of 350 and (b) 10 wt % of a second comprising a 65 wt % ZSM-12:35 wt % $Al_2O_3$ extrudate impregnated with 0.1 wt % Pt. Details and results of the tests are summarized in Table 3 and show significantly higher light gas make with the non-aromatic containing feed and higher hydrogen consumption with the non-aromatic containing feed.

TABLE 3

| Feed Composition (wt %) | | |
|---|---|---|
| methylcyclopentane | 2.34 | 0.00 |
| n-heptane | 4.21 | 0.00 |
| 2,3-dimethylpentane | 2.76 | 0.00 |
| methylcyclohexane | 2.41 | 0.00 |

TABLE 3-continued

|  |  |  |  |  |
|---|---|---|---|---|
| nonane | 4.31 | 0.00 |  |  |
| Other Non-Aromatics | 0.33 | 0.30 |  |  |
| Total Non-Aromatics | 16.37 | 0.31 |  |  |
| Benzene | 0.01 | 0.02 |  |  |
| Toluene | 16.31 | 18.24 |  |  |
| C8 Aromatics | 0.12 | 0.13 |  |  |
| C9 Aromatics incl. indane | 49.70 | 61.80 |  |  |
| C10 Aromatics, excl. naphthalenes | 16.68 | 18.64 |  |  |
| C11+ Aromatics, exc. Naphthalenes | 0.48 | 0.51 |  |  |
| Naphthalene | 0.23 | 0.25 |  |  |
| M-naphthalenes | 0.09 | 0.10 |  |  |
| Total Aromatics | 83.63 | 99.69 |  |  |
| Operating Conditions |  |  |  |  |
| Pressure (psig) | 347 | 347 | 347 | 347 |
| WHSV (1/hr) | 2.0 | 3.0 | 2.0 | 3.0 |
| Bed Inlet Temp (° F.) | 752 | 752 | 752 | 752 |
| Average RX T (° F.) | 809 | 807 | 794 | 783 |
| Reactor DT (° F.) | 73 | 74 | 58 | 45 |
| H2/HC Molar Ratio | 3.0 | 3.0 | 3.0 | 3.0 |
| NA Conversion (%) |  |  |  |  |
| Methlcyclopentane | 99 | 98 | N/A | N/A |
| n-heptane | 100 | 98 | N/A | N/A |
| 2,3-dimethylpentane | 79 | 64 | N/A | N/A |
| Methylcyclohexane | 100 | 99 | N/A | N/A |
| Nonane | 100 | 100 | N/A | N/A |
| Overall Non-Aromatics | 94 | 89 | N/A | N/A |
| Product Yields (wt %) |  |  |  |  |
| Hydrogen | −0.96 | −0.77 | −0.65 | −0.49 |
| Methane | 0.33 | 0.26 | 0.10 | 0.07 |
| Light Gas (C5−, incl. C1) | 24.30 | 22.55 | 10.18 | 8.03 |
| NA's | 1.00 | 1.73 | 0.12 | 0.17 |
| Benzene | 4.23 | 3.96 | 5.52 | 4.88 |
| Toluene | 18.31 | 71.22 | 21.79 | 20.38 |
| Ethylbenzene | 1.23 | 1.57 | 2.24 | 2.94 |
| Xylenes | 24.88 | 23.17 | 26.35 | 21.55 |
| C9 Aromatics | 17.52 | 19.32 | 21.43 | 26.49 |
| C10 Aromatics | 5.71 | 7.13 | 8.38 | 11.10 |
| C11+ Aromatics | 3.78 | 4.13 | 4.64 | 4.95 |

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of may be substituted therefor.

What is claimed is:

1. A hydrocarbon upgrading process comprising:
   (a) treating a hydrocarbon feed in at least one of a steam cracker, catalytic cracker, coker, hydrocracker, and reformer under suitable conditions to produce a first stream comprising aliphatic and aromatic hydrocarbons;
   (b) recovering from said first stream a second stream composed mainly of $C_6$ to $C_9$ aliphatic and aromatic hydrocarbons;
   (c) separating at least part of the second stream into a overhead stream containing $C_7-$ hydrocarbons and a bottoms stream containing $C_8+$ hydrocarbons;
   (d) removing aliphatic hydrocarbons from said overhead stream to produce an aliphatic hydrocarbon-depleted $C_7-$ stream;
   e) feeding said aliphatic hydrocarbon-depleted $C_7-$ stream, said bottoms stream containing $C_8+$ hydrocarbons, and hydrogen to a first reaction zone containing a catalyst system effective to dealkylate $C_8+$ single-ring aromatic hydrocarbons having at least one alkyl group containing two or more carbon atoms and transalkylate $C_8+$ single-ring aromatic hydrocarbons having at least two methyl groups and produce a third stream having an increased toluene content or increased toluene and increased benzene content compared with said aliphatic hydrocarbon-depleted $C_7-$ stream and said bottoms stream containing $C_8+$ hydrocarbons; and
   (f) methylating benzene and/or toluene from said third stream with a methylating agent to produce a xylene-enriched stream.

2. The process of claim 1, further comprising hydrotreating the second stream before the said separating (c).

3. The process of claim 1, wherein said aliphatic hydrocarbons are separated in (d) by solvent extraction or selective adsorption.

4. The process of claim 1, wherein the second stream is hydrotreated to reduce the content of olefins, diolefins, and acetylenes prior to (d).

5. The process of claim 1, wherein the catalyst in (e) comprises at least a first and second catalyst composition, wherein the first catalyst composition comprises a first molecular sieve having a Constraint Index in the range of about 3 to about 12 and at least one metal or compound thereof of Groups 6 to 10 of the Periodic Table of the Elements, and wherein the second catalyst composition comprising a second molecular sieve having a Constraint Index less than 3 and at least one metal or compound thereof of Groups 6 to 10 of the Periodic Table of the Elements.

6. The process of claim 5, wherein said first molecular sieve comprises at least one of ZSM-5, ZSM-11, ZSM-22, ZSM-23, ZSM-35, and ZSM-48.

7. The process of claim 5, wherein said first molecular sieve has an alpha value in the range of 100 to 1500.

8. The process of claim 5, wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20.

9. The process of claim 5, wherein said second molecular sieve has an alpha value in the range of 20 to 500.

10. The process of claim 5, wherein said first molecular sieve is ZSM-5 and said second molecular sieve is ZSM-12.

11. The process of claim 1, wherein said methylating agent is methanol.

12. The process of claim 1, further including (g) recovering para-xylene from said xylene-enriched stream.

13. The process of claim 12, further comprising recycling at least part of said para-xylene-depleted stream to (d).

14. The process of claim 1, wherein the hydrocarbon feed is selected from natural gas liquids, natural gas condensate, naphtha, distillate, gas oils, crude oils, and/or resids.

15. The process of claim 1, wherein said aliphatic hydrocarbons removed in (d) are recovered for use as a gasoline blending component.

16. The process of claim 1, wherein said methylating of toluene or methylating of benzene and toluene is para-selective.

17. The process of claim 1, further comprising feeding additional benzene to (e).

18. The process of claim 17, wherein at least part of said additional benzene is removed from said third stream.

* * * * *